United States Patent
Romans

(10) Patent No.: US 6,618,492 B1
(45) Date of Patent: Sep. 9, 2003

(54) SYSTEM AND METHOD FOR MEASUREMENT OF ADHESIVE RESIN DISTRIBUTION ON WOOD FLAKES USING A SCANNER

(75) Inventor: James E. Romans, Brookeland, TX (US)

(73) Assignee: Georgia-Pacific Resins, Inc., Atlanta, GA (US)

( * ) Notice: Subject to any disclaimer, the term of this patent is extended or adjusted under 35 U.S.C. 154(b) by 0 days.

(21) Appl. No.: 09/603,995

(22) Filed: Jun. 26, 2000

(51) Int. Cl.[7] ............................................. G06K 9/00
(52) U.S. Cl. ..................... 382/108; 382/274; 382/300; 382/312; 427/8; 427/464; 428/104; 428/394; 428/528; 156/64
(58) Field of Search .............................. 382/100, 108, 382/109, 143, 274, 300, 312; 427/8, 446, 464; 252/1, 408.1, 301.16, 700; 428/104, 106, 114, 361, 378, 394, 411.1, 528, 402, 535, 407; 156/64

(56) References Cited

U.S. PATENT DOCUMENTS

| | | | |
|---|---|---|---|
| 4,543,602 A | | 9/1985 | Kai et al. |
| 4,820,932 A | | 4/1989 | Miller |
| 4,868,403 A | | 9/1989 | Takahashi et al. |
| 5,164,844 A | | 11/1992 | Granger |
| 5,298,974 A | | 3/1994 | Chandley |
| 5,635,248 A | * | 6/1997 | Hsu et al. .................... 427/358 |
| 5,663,569 A | | 9/1997 | Hayano |
| 5,719,939 A | | 2/1998 | Tel |
| 5,787,186 A | | 7/1998 | Schroeder |
| 5,841,539 A | | 11/1998 | Ikurumi et al. |
| 5,907,413 A | | 5/1999 | Han |
| 5,912,974 A | | 6/1999 | Holloway et al. |
| 6,122,065 A | * | 9/2000 | Gauthier ..................... 356/394 |

OTHER PUBLICATIONS

Chem Abs vol. 103, p. 034335.
Journal of Applied Crystallogr 1991, vol. 24 (pt1) p. 73–4.
Holz Roh Werkst, 1994 vol. 52(2) p. 119–125.
Forest Products Journal, ISSN 0015–7473 products research society 1980 vol. 30(7) p. 37–40.
Proc. Symp Particleboard, 19787 vol. 11 p. 101–129.
Holz Roh Werkst, 1970 vol. 28(8) p. 289–92.
Kem Ind., 1966, vol. 15(12) p. 743–4.
Journal of Adhesion, Johnson, S.E. et al., 1992 vol. 40(1) p. 47–61.

* cited by examiner

Primary Examiner—Jayanti K. Patel
Assistant Examiner—Sheela Chawan
(74) Attorney, Agent, or Firm—Banner & Witcoff, Ltd.

(57) ABSTRACT

The present invention provides a system and method for determining adhesive resin distribution on wood flakes to be formed into a wood-based composite. Where a predetermined amount of adhesive resin has been sprayed onto a selected amount of wood flakes being tumbled in a blender, the method includes the steps of: removing a sample of sprayed wood flakes at the output of the blender and placing the sprayed wood flakes on a scanning bed; scanning the sprayed wood flakes with a scanner having at least 1200 dpi resolution with 1800 dpi interpolation to provide image data; using image analysis software with resin analysis macros to filter the image data to provide a high contrast image that shows each adhesive resin spot differentiated from the wood flake on which the adhesive resin spot is situated; and measuring and analyzing the high contrast image to provide an output showing at least a percent coverage of the wood flake by the adhesive resin.

17 Claims, 6 Drawing Sheets

NEW SCANNER SYSTEM~16X

EAGLE ANALYTICAL RDM 50X THROUGH MICROSCOPE

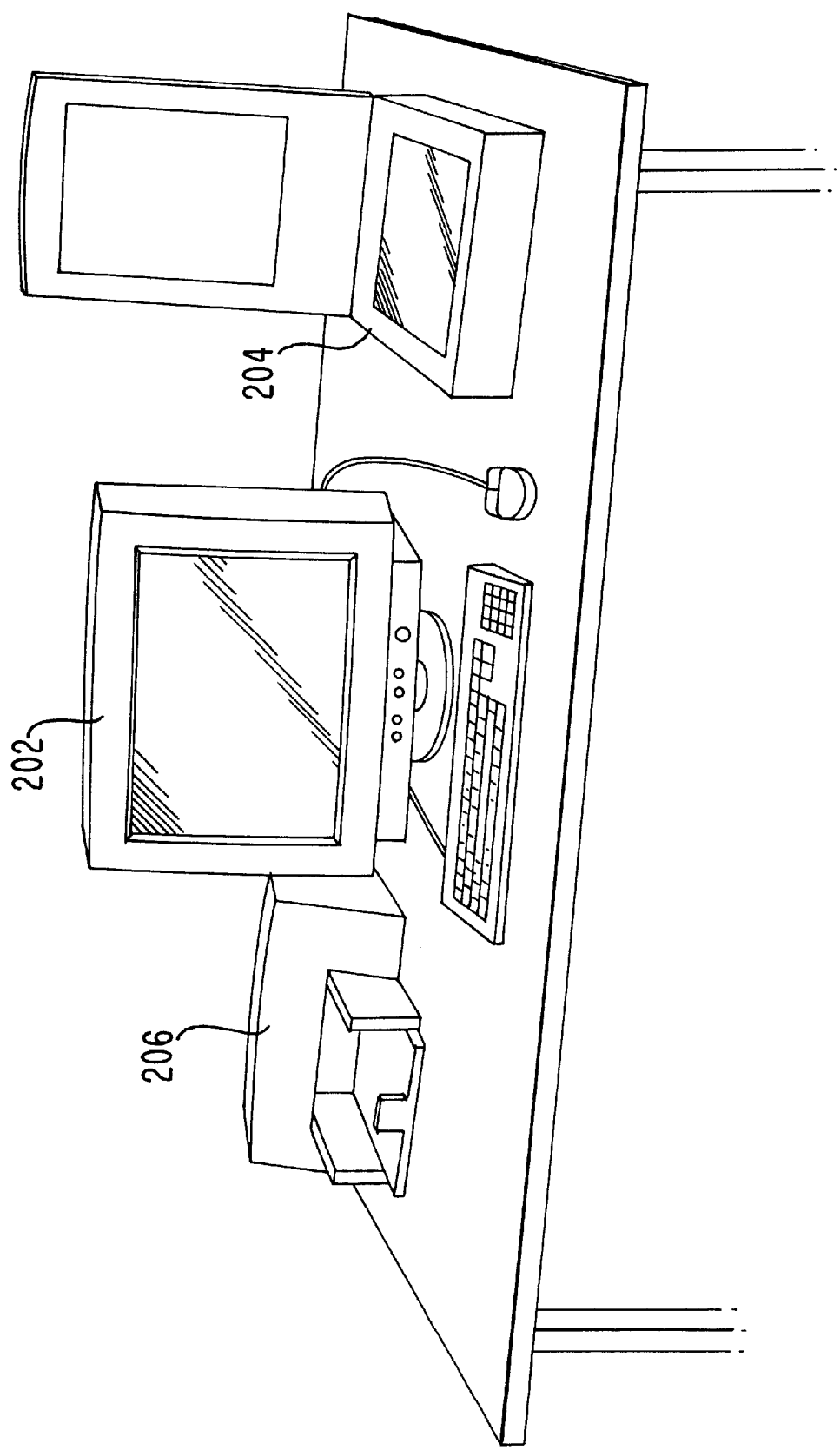

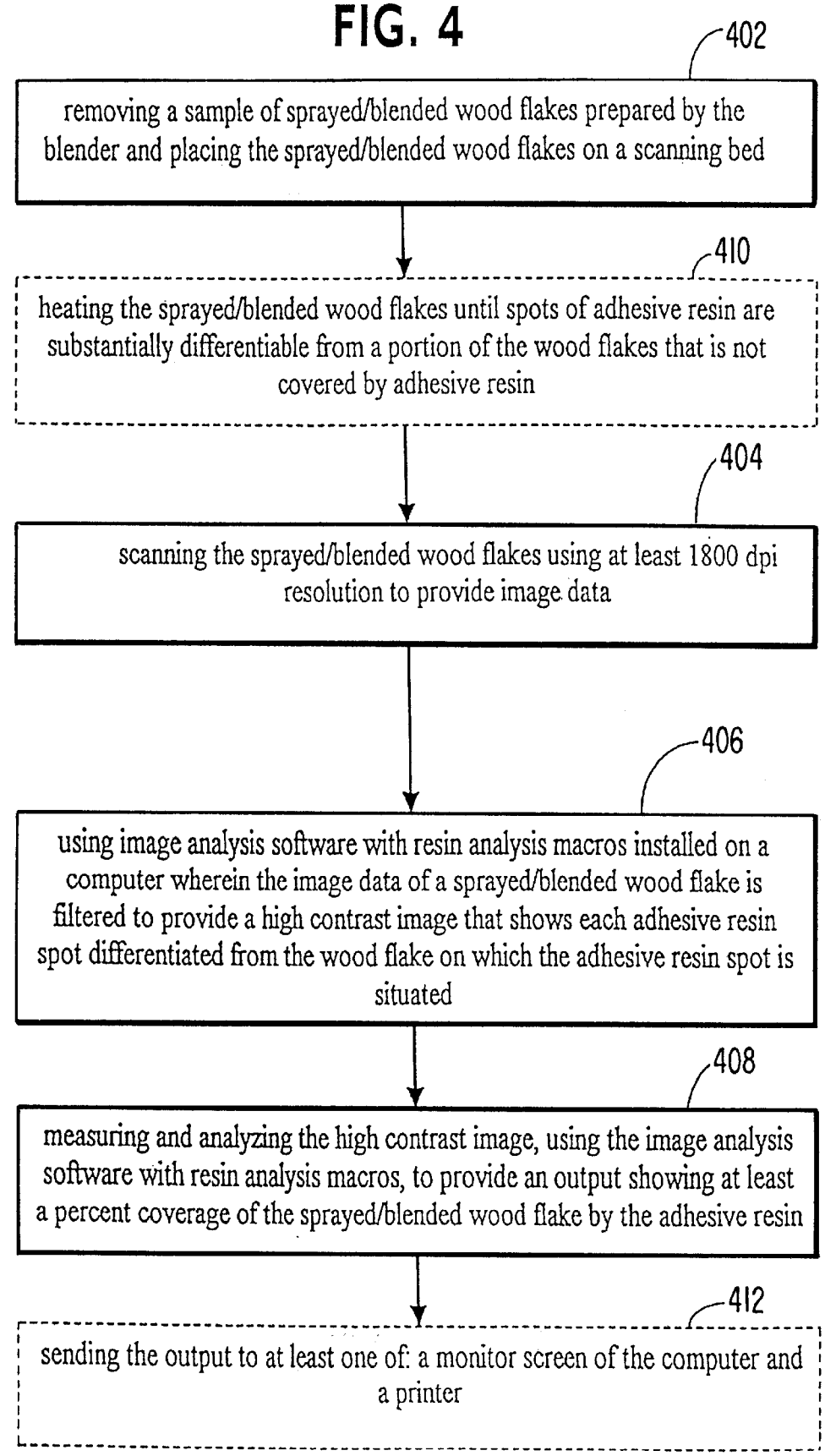

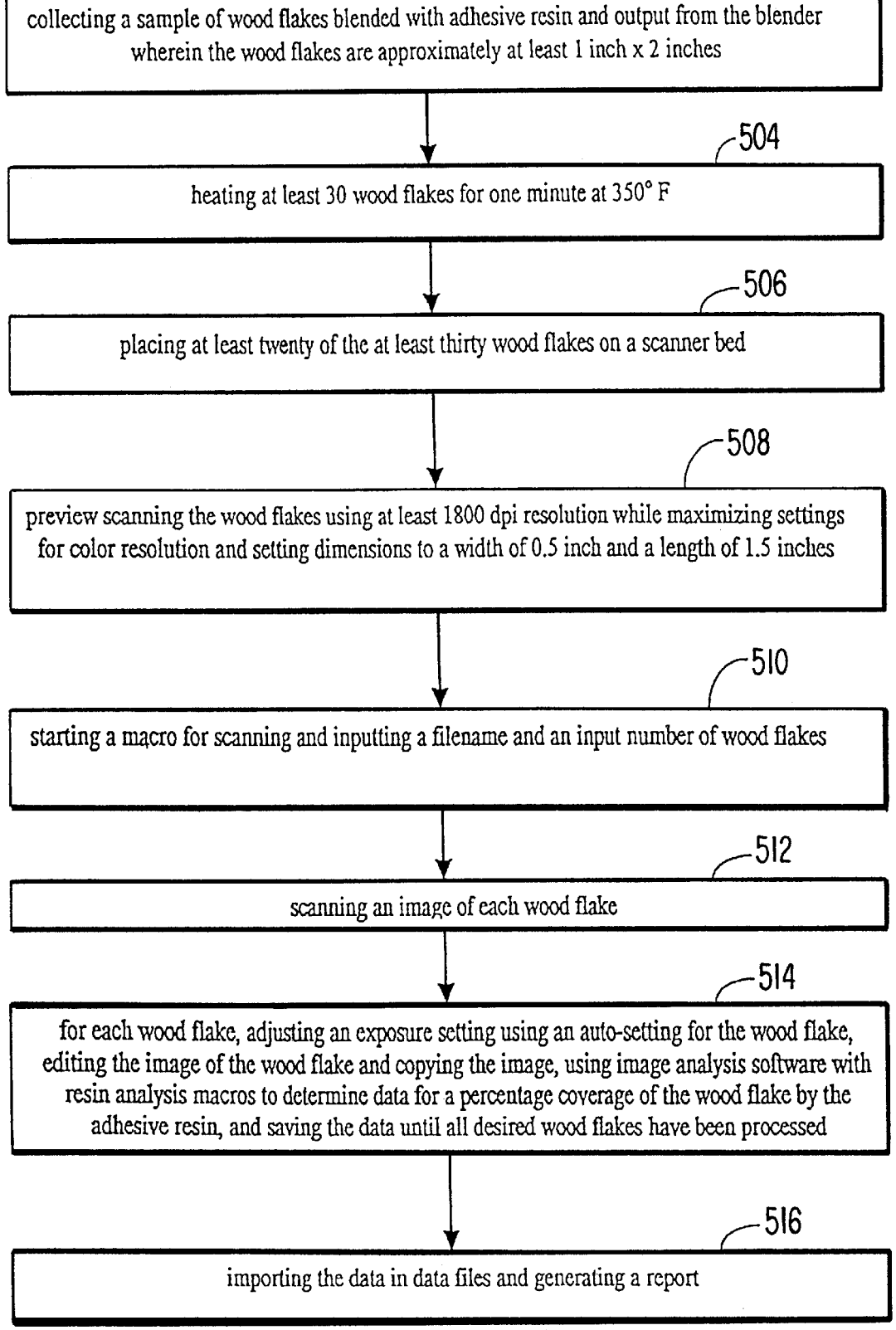

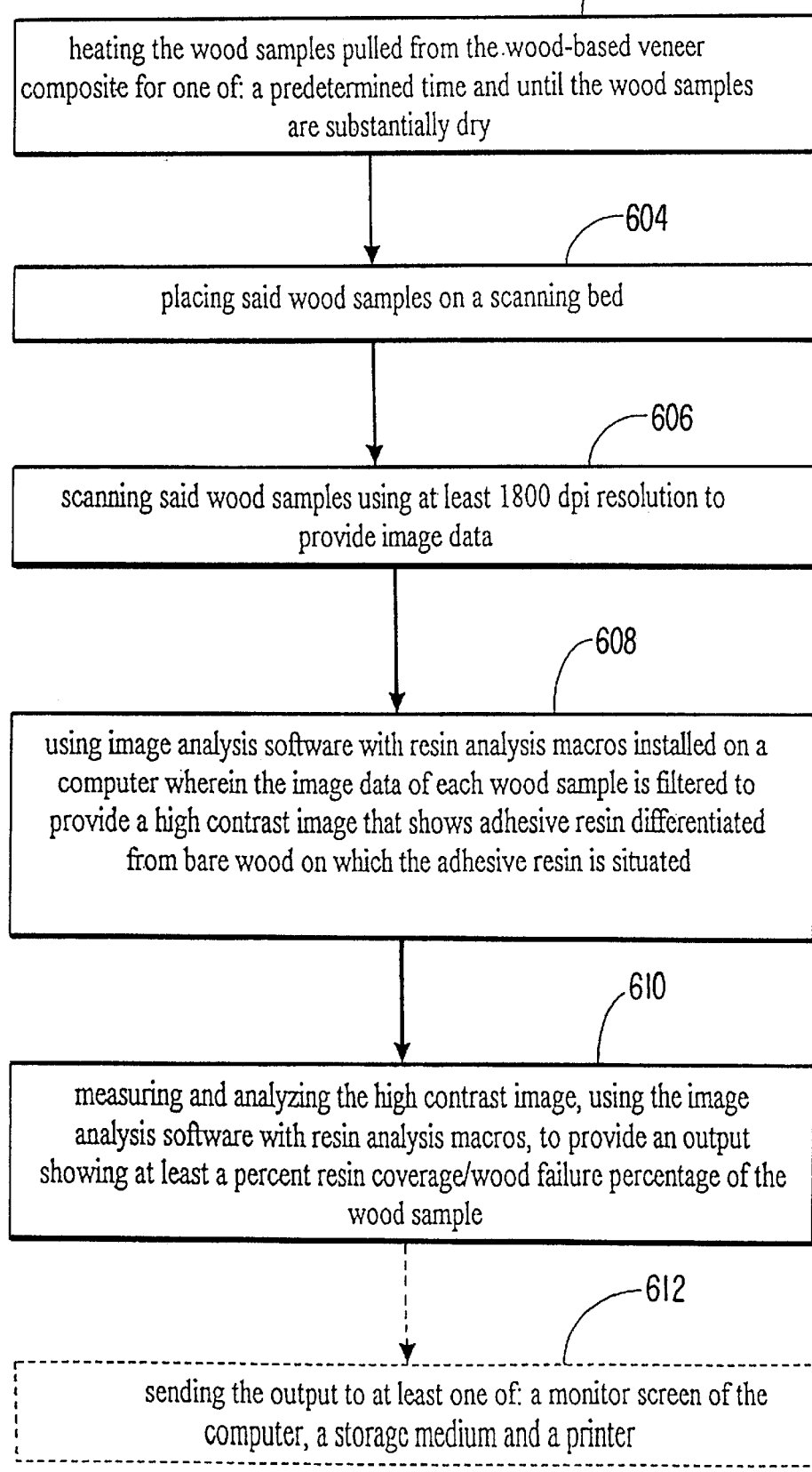

SYSTEM AND METHOD FOR MEASUREMENT OF ADHESIVE RESIN DISTRIBUTION ON WOOD FLAKES USING A SCANNER

FIELD OF THE INVENTION

The present invention relates generally to measuring the blending efficiency of an adhesive resin with wood flakes and more particularly, to a system for measuring adhesive resin distribution on the wood flakes.

BACKGROUND OF THE INVENTION

Many wood-based composite materials are in use for construction of homes, furniture and various products. These composite materials are generally available in sheet or panel form. Conventional composites are generally produced by adding a heat-curing adhesive resin composition to wood fibers and pressing the wood fibers together to form the sheet or panel.

Wood fiber is processed similarly for particle and fiber materials to prepare the end product of wood-based composite material. The wood fiber is flaked or chipped from wood, typically logs. Wood may be reduced to particles or strands. Wood chips may be steamed to soften the wood and reduce its composition to fibers. Fiberboard, Oriented Strandboard (OSB), and waferboard are generally prepared by drying the wood fibers or flakes/chips, adding an adhesive resin, and placing on a surface as a mat. The mat is pressed, generally by a platen-type press using heat and pressure to cure the adhesive resin. The wood particles, strands or fibers become bonded by the adhesive resin, and the bonded wood-based composite may then be cut to a desired size.

Waferboard was originally made from aspen. As the wood-based composite industry grew, Oriented Strandboard (OSB), a wood-based composite that included other hardwoods became the main wood-composite material. OSB is generally prepared from thin hardwood or pine strands that are aligned in a selected direction, then bonded together with waterproof adhesive resin using heat and pressure. The aligned or "oriented" strands provide better strength than the original products of waferboard. The OSB may be used, for example, for walls, roofs, and floor covering material in commercial building and home construction.

Often, wood flakes are tumbled in a blender with adhesive resin, allowing the adhesive resin to coat the wood flakes so that, upon applying pressure and heat to a mat of the resin-coated flakes, the adhesive resin will bond the flakes, forming the desired wood-based composite. Typically, in order to assess the sufficiency of the blending, samples of the wood flakes have been taken from the blended mixture, and then the samples were examined using high magnification and/or special lighting and special cameras. While these methods were better than a simple visual analysis, these types of systems have generally required special care and have been very expensive to repair and use at multiple locations.

Current systems for determining the sufficiency of the adhesive resin coverage of the wood flakes employ the use of a microscope and a video camera or video camera and magnifier. These systems are expensive and take an hour and a half to two hours to complete measurement of a sample. For example, an RDM system from Eagle Analytical, Blackburg, Va. costs about $40,000. A system from Forintek, Ottawa, Ontario, Canada, costs approximately $25,000.

Thus, there remains a strong need for a method and system for providing inexpensive and efficient measurement of the sufficiency of the adhesive resin application to the wood substrate (e.g., how much adhesive resin is distributed onto the wood flakes) in order to facilitate the effective operation of a wood-based composite bonding process and to provide a more uniform wood-based bonded composite product.

SUMMARY OF THE INVENTION

The present invention provides a method for determining adhesive resin distribution/percentage of area covered on wood flakes that are to be formed into a wood-based composite. A predetermined amount of adhesive resin is generally sprayed onto a selected amount of wood flakes being tumbled in a blender prior to heat compression of the sprayed/blended wood chips into a wood-based composite. The method includes, after tumbling the sprayed/blended wood flakes in the blender, removing a sample of sprayed/blended wood flakes provided by the blender and placing the sprayed/blended wood flakes on a scanning bed, scanning the sprayed/blended wood flakes with a scanner having at least 1200 dpi (dots per inch) resolution with 1800 dpi interpolation to provide image data, using image analysis software with resin analysis macros that are installed on a computer to filter the image data to provide a high contrast image that shows each adhesive resin spot differentiated from uncoated wood flake on which the adhesive resin spot is situated, and measuring and analyzing the high contrast image to provide an output showing at least a percent coverage of the sprayed/blended wood flake by the adhesive resin.

The method may further include, after removing the sample of sprayed wood flakes, heating the sprayed/blended wood flakes until spots of adhesive resin are substantially differentiable from the portion of the wood flakes not covered by the adhesive resin. For example, the sample of wood flakes removed from the blender may be heated at 250° F. for a predetermined time such as 15–45 minutes before scanning. Measuring and analyzing the high contrast image generally includes: determining an area of the adhesive resin spot/spots, determining an area of the wood flake on which the spot/spots are situated, determining a percent coverage of the area of the wood flake by the spot/spots, and determining an average percent coverage area of a preselected number of wood flakes by the adhesive resin spots.

The present invention also provides a system for determining adhesive resin distribution on blended wood flakes for wood-based composite production. The system includes a flatbed scanner and image analysis software with resin analysis macros that are installed on a computer. The flatbed scanner generally has at least 1200 dpi resolution with 1800 dpi interpolation and is arranged to receive a sample of the blended wood flakes, typically obtained from the output of a blender. The flatbed scanner scans the blended wood flakes to provide image data to image analysis software with resin analysis macros installed on a computer. The image analysis software with resin analysis macros receives the image data from the flatbed scanner and filters the image data to provide a high contrast image that shows each adhesive resin spot differentiated from the wood flake not having a resin coating on which the adhesive resin spot is situated, measures an area of each adhesive resin spot and the area of the uncovered wood flake on which the adhesive resin spot is located and analyzes the image data to provide an output showing at least a percent coverage of the wood flake by the adhesive resin. Where desired, the sample of sprayed wood flakes obtained from the blender may be heated, for example at 250° F. for a predetermined time, until spots of adhesive resin are substantially differentiable from the uncovered region of the wood flakes. Typically, the sprayed/blended wood flakes may be heated for 15–45 minutes. Generally, the output may be displayed on a computer monitor and/or printed.

The method may be used for determining adhesive resin distribution on wood samples pulled from a wood-based veneer composite that has been water-soaked for a predetermined amount of time, in order to examine wood failure/ glue failure to provide a grade for the wood-based veneer composite. The method includes the steps of: heating the wood flakes pulled from the wood-based veneer composite for one of: a predetermined time and until the wood flakes are substantially dry; placing said wood flakes on a scanning bed; scanning said wood flakes using at least 1200 dpi resolution with 1800 dpi interpolation to provide image data; using image analysis software with resin analysis macros installed on a computer wherein the image data of each wood sample is filtered to provide a high contrast image that shows adhesive resin differentiated from bare wood on which the adhesive resin is situated; and measuring and analyzing the high contrast image, using the image analysis software with resin analysis macros, to provide an output showing at least a percent resin coverage/grade of the wood sample.

BRIEF DESCRIPTION OF THE DRAWINGS

FIG. 2 shows a schematic drawing of one embodiment of a system for implementing the method of the present invention.

FIG. 4 is a flow chart showing one embodiment of steps in accordance with the method of the present invention.

FIG. 5 is a flow chart showing another embodiment of steps in accordance with the method of the present invention.

FIG. 6 is a flow chart showing one embodiment wherein the method of the present invention is used for determining wood failure percentage on wood samples pulled from a wood-based veneer composite that has been vacuum/water- soaked for a predetermined amount of time, to provide a grade for the wood-based veneer composite.

DETAILED DESCRIPTION OF THE PREFERRED EMBODIMENTS

The present invention provides an efficient, inexpensive process for determining adhesive resin coverage (e.g., percent coverage) and spot size on wood flakes that have been sprayed with the adhesive resin to promote bonding when the wood flakes are heat-compressed to form a wood-based composite material. Using a high-resolution computer-based scanner and a computer with image analysis software, adhesive resin-coated wood flakes, especially wood flakes that have been heat-treated to enhance resolution of the resin spot images, may be scanned and the resin spot size, the resin coverage percentage as well as the coverage percentage variation between flakes may be determined within a period of about 20 minutes.

In the past, the difficulty in time and expense required to measure the blending efficiency of adhesive resin on wood flakes has made optimizing wood flake and adhesive resin blending a somewhat subjective process when dealing with a production or a lab setting. In recent years, use of high magnification, special lighting and special cameras to measure adhesive resin on wood flakes has provided better estimations than simple visual analysis, such means, however, have required special care and high expense. Applicants have discovered that the more recently developed computer scanners, having a higher resolution than was available in the past, provide a cost effective alternative to such prior art analysis tools. The present invention utilizes such state-of-the-art computer scanners to provide an effective magnification that allows one to differentiate between adhesive resin spots and wood fiber. In addition, a preferred feature of the present invention, especially where the uncured resin color is not as differentiable from the wood fiber as desired, involves heating the adhesive resin-blended wood flakes before scanning to cause the adhesive resin spots on the wood to darken, thus providing a more readily differentiable image of the spot and the un-coated wood flake.

Figure 1B:
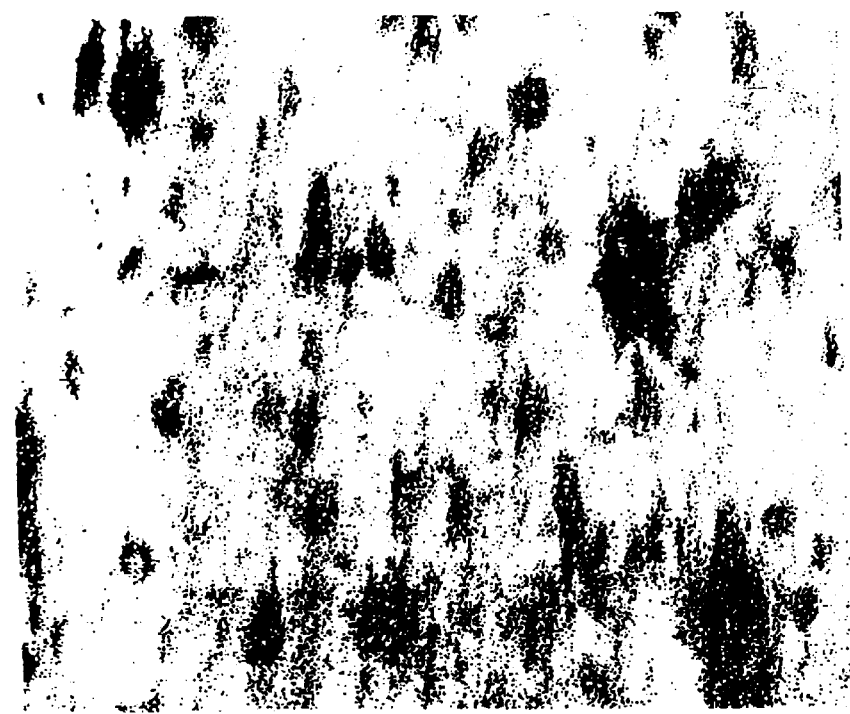
FIG. 1B shows a representation of an image of blended/ sprayed wood flakes using the method of the present invention with 16× magnification.
Figure 1A:
FIG. 1A shows a representation of an image of blended/ sprayed wood flakes using an Eagle Analytical RDM 50× magnification.

An example of the output of an image of blended/sprayed wood flakes viewed using a prior art Eagle Analytical RDM® 50× magnification is shown in FIG. 1A. An example of an image of blended/sprayed wood flakes made using the scanning method of the present invention with 16× magnification is shown in FIG. 1B.

A typical test system for implementing the present invention includes a desktop computer with a high speed processor, at least 128 megabytes of RAM, a video card capable of 1600×1200 resolution and a monitor capable of 1600×1200 resolution, image analysis software, spreadsheet software (e.g., Excel®), and a high resolution computer scanner capable of providing an image with 1200 dpi resolution with 1800 dpi interpolation.

As shown in FIG. 2, in one embodiment the following hardware and software may be utilized to implement the present invention: a 350 MHz computer, Pentium® class, with 128 megabytes of RAM and a hard drive (attached to the monitor, but not visible in FIG. 2), a video card and monitor 202 capable of 1600×1200 true color resolution, a Hewlett-Packard Scanjet 6200C® Flatbed Scanner 204, Media Cybernetics Image Pro Plus® image analysis software (installed in computer, but not visible in FIG. 2), Microsoft Excel97® spreadsheet (installed in computer, but not visible in FIG. 2), custom macros as described below for Image Pro Plus® and Excel97® (installed, but not visible in FIG. 2), and an inkjet printer 206. The custom macros are resin analysis macros that are software programs that use the measurements obtained by the image analysis software to generate desired data in a desired format, such as, for example, the format shown in the table below. Generally, wood flakes are tumbled in an adhesive resin blender, which may, for example, be ten feet in diameter and 25–30 feet long. Such blenders are well known to those skilled in the art of manufacturing wood composites from wood substrate material, such as wood chips. The blender typically has a spray nozzle mounted in the blender to spray the adhesive resin onto the tumbling flakes. At the exit of the blender, typically a handful of resin-coated wood flakes is extracted, is placed in a tray and where desired, is heated until the resin spots show a desired amount of contrast with the color of the wood substrate. The wood flakes to be tested are then placed on the scanning bed. Image analysis software is then started, and the scanning software is activated. Image analysis software (Image Pro Plus®) from Media Cybernetics, 8484 Georgia Avenue, Suite 200, Silver Spring, Md. 20910 (email: info@mediacy.com) was obtained for implementation of a preferred embodiment. In a preferred embodiment, the scanner software is set as follows:

| Output Type | TrueColor |
|---|---|
| DPI | 1800 |
| Selection Area Dimensions | 1.5 W × 0.5 H |
| Color Adjustment Saturation | 50 |
| Sharpen Level | Extreme |
| Exposure Adjustment | Auto for each flake |

The image software is set to have a screen calibration of Pixels/Unit=0.070557508. The scanner area box is then moved so that the image of the flake to be tested is obtained by the scanner. The image is then copied to the clipboard and is pasted to the image software. Filtering is set to a value that provides a high contrast image, and the measurement tool in the image software is used to analyze the resin spots and the uncoated wood substrate. The resultant data may be further analyzed for spot size and coverage percentage. The following table is an example of one set of data that may be generated using the present invention:

| Run Ord | 4 | 7 | 1 | | 9 | 12 | 3 | 11 | 2 | 5 | 10 | 6 | | | |
|---|---|---|---|---|---|---|---|---|---|---|---|---|---|---|---|
| Test Ord | 1 | 2 | 3 | 4 | 5 | 6 | 7 | 8 | 9 | 10 | 11 | 12 | Ave | Std Dev | % Cov |
| 1 | 17.4 | 2.7 | 4.3 | 8.7 | 17.8 | 4.9 | 4.7 | 5.5 | 18.2 | 5.7 | 3.9 | 26.2 | 10.0 | 6.54 | 65.5 |
| 2 | 19.4 | 1.7 | 4.8 | 8.0 | 19.1 | 4.5 | 4.3 | 5.7 | 18.8 | 5.7 | 3.9 | 29.1 | 10.4 | 7.31 | 70.2 |
| 3 | 18.4 | 1.9 | 4.6 | 9.4 | 17.8 | 6.2 | 5.0 | 6.2 | 17.6 | 5.1 | 3.7 | 29.1 | 10.4 | 6.49 | 62.3 |
| 4 | 17.4 | 1.6 | 5.4 | 8.9 | 17.8 | 4.9 | 5.0 | 5.0 | 18.8 | 5.7 | 4.2 | 28.3 | 10.3 | 6.69 | 65.2 |
| 5 | 18.4 | 1.8 | 4.6 | 7.3 | 18.5 | 4.9 | 5.4 | 6.0 | 20.7 | 7.4 | 4.2 | 29.1 | 10.7 | 7.26 | 68.0 |
| 6 | 19.4 | 1.8 | 5.4 | 7.3 | 19.1 | 4.9 | 5.4 | 5.7 | 18.8 | 7.7 | 3.6 | 29.1 | 10.7 | 7.16 | 67.1 |
| 7 | 17.4 | 1.6 | 5.4 | 7.8 | 21.1 | 5.3 | 4.7 | 6.0 | 19.4 | 7.0 | 3.9 | 30.5 | 10.8 | 7.32 | 67.6 |
| 8 | 17.4 | 1.8 | 5.8 | 6.9 | 17.2 | 5.1 | 4.0 | 5.7 | 23.4 | 6.6 | 4.2 | 31.2 | 10.8 | 7.58 | 70.3 |
| 9 | 16.9 | 1.9 | 4.3 | 7.8 | 19.7 | 4.5 | 4.7 | 6.0 | 21.4 | 6.0 | 4.6 | 29.8 | 10.6 | 7.48 | 70.5 |
| 10 | 17.9 | 2.8 | 5.6 | 8.2 | 19.1 | 5.3 | 5.2 | 6.0 | 19.4 | 7.0 | 4.6 | 29.8 | 10.9 | 6.79 | 62.3 |
| Ave | 1.0 | 2.0 | 5.0 | 8.0 | 18.7 | 5.1 | 4.8 | 5.8 | 19.7 | 6.4 | 4.1 | 29.2 | | | |
| Std Dev | 0.90 | 0.43 | 0.55 | 0.77 | 1.13 | 0.49 | 045 | 0.32 | 1.72 | 0.88 | 0.34 | 1.35 | | | |
| % Cov | 5.0 | 21.7 | 10.9 | 9.7 | 6.1 | 9.6 | 9.3 | 5.6 | 8.7 | 13.8 | 8.3 | 4.6 | | | |
| Min | 16.9 | 1.6 | 4.3 | 6.9 | 17.2 | 4.5 | 4.0 | 5.0 | 17.6 | 5.1 | 3.6 | 26.2 | | | |
| Max | 19.4 | 2.8 | 5.8 | 9.4 | 21.1 | 6.2 | 5.4 | 6.2 | 23.4 | 7.7 | 4.6 | 31.2 | | | |

In the above table, the results of percent coverage of twelve wood flakes by adhesive resin is measured ten times: Test Ord represents Test Order and Run Ord represents Run Order; Std Dev represents standard deviation, and % Cov represents the percent coverage of a wood flake by the adhesive resin. The flakes that are being measured are numbered 1–12 horizontally in line two of the table. It should be noted that the image data for each flake tend to be reproducible, and the method may be implemented quickly and inexpensively.

Clearly, based on the measurements obtained, the user may determine whether a greater/smaller area of the wood flakes discharged from the blender is desired to be covered with adhesive resin, and alter the blender settings, such as rate of mixing, rate of adhesive resin spray, etc., to adjust the amount of adhesive resin being applied to the wood proportionately in accordance with the desired increase/decrease in area coverage. After making the adjustment in the blender setting(s), such as spraying rate, and allowing the wood flakes already sprayed at the former spray rate to clear the blender, the adhesive resin-coated wood flakes being prepared using the adjusted settings, such as by adjusting the spraying amount of adhesive resin, may be sampled and tested in the manner described above to check to see that the desired area coverage is being obtained.

Figure 3:
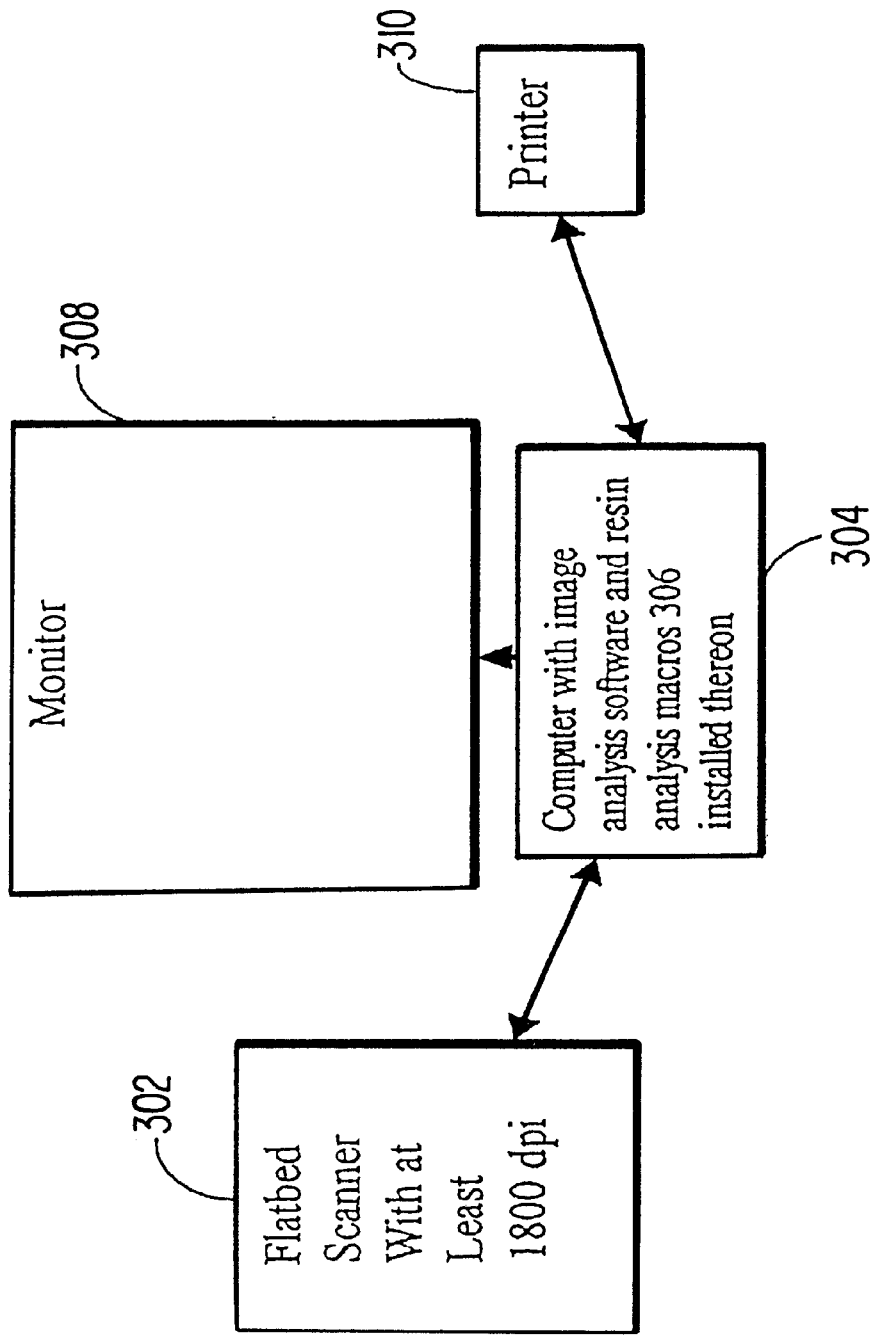
FIG. 3 is a block diagram of one embodiment of a system in accordance with the present invention.

FIG. 3 is a block diagram of one embodiment of a system in accordance with the present invention. The invention provides a system for determining adhesive resin distribution on blended wood flakes that are to be used for wood-based composite production. The system includes at least a flatbed scanner 302 with at least 1200 dpi resolution and 1800 dpi interpolation, that is coupled to a computer 304 having image analysis software with resin analysis macros 306 installed thereon. The computer 304 typically is at least a 350 MHz computer, preferably Pentium® class, with at least 128 megabytes of RAM and a video card with at least 1600×1200 resolution. A sample of adhesive resin blended wood flakes is taken from a resin blender (not shown) that is used to apply, e.g., spray, adhesive resin on the wood flakes. Generally, the sample is taken at the output of the blender. The flatbed scanner 302 scans the adhesive resin blended wood flakes and provides image data to the computer 304 that utilizes image analysis software that includes resin analysis macros 306 installed on the computer 304. The image analysis software filters the image data to provide a high contrast image that shows each adhesive resin spot differentiated from the bare, uncoated wood flake on which the adhesive resin spot is situated, and in accordance with the resin analysis macros, measures an area of each adhesive resin spot and the area of any bare wood flake on which the adhesive resin spot is located and analyzes the image data to provide at least a percent coverage of the wood flake by the adhesive resin. Where desired, the sample of sprayed/blended wood flakes may be heated until spots of adhesive resin are substantially differentiable from the wood flakes, i.e., increasing the contrast between areas of the wood covered with adhesive resin and uncoated areas. The heating thus provides a more differentiable image for measurement of the extent/sufficiency of adhesive resin application onto the wood. For example, the sample of sprayed/blended wood flakes may be heated at 250° F. for a predetermined time prior to being scanned. A typical predetermined time for the heating the adhesive resin blended wood may be from about 15 minutes to 45 minutes. Generally, the image may be measured to determine an average percent coverage area of a preselected number of wood flakes by the adhesive resin spots. The measurements, error deviations, averages and the like (as for example, shown in the table above) may be shown on the monitor 308 of the computer, mare be stored on a suitable storage medium and/or may be printed out at a printer 310.

FIG. 4 is a flow chart showing one embodiment of operative steps for practicing the scanning of adhesive-coated wood in accordance with the method of the present invention. The method provides for determining adhesive resin distribution on wood flakes (strands) that are to be formed into a wood-based composite. Generally, as is known in the art, the wood flakes are tumbled in an adhesive resin blender that sprays the tumbling wood flakes with an adhesive resin prior to heat compression of the flakes to prepare, for example, OSB. Since the flow rate of the sprayer in the blender that is spraying the adhesive resin is known and the amount/weight of the wood flakes passing through the blender per unit time is known, once a determination of the approximate surface area of the wood flakes that is being covered by the adhesive resin has been made, the amount of adhesive resin being sprayed onto the wood flakes may be adjusted to achieve a desired percentage of coverage of the area of the wood flakes so that the wood flakes can be heat compressed to obtain the desired product using a desired amount of adhesive/unit area to bind the wood flakes to form the composite wood product. Typically, the method includes removing a sample of adhesive resin sprayed/blended wood flakes prepared by the blender and then placing the sprayed/blended wood flakes on a scanning bed 402, scanning 404 the sprayed/blended wood flakes using at least 1200 dpi resolution and 1800 dpi interpolation to obtain image data, using image analysis software with resin analysis macros 406 installed on a computer wherein the image data of an adhesive resin sprayed/blended wood flake is filtered to provide a high contrast image that shows each adhesive resin spot differentiated from the bare wood flake on which the adhesive resin spot is situated, and measuring and analyzing 408 the high contrast image using the image analysis software with resin analysis macros to provide an output showing at least a percent coverage of the sprayed/blended wood flake by the adhesive resin. Where desired, the method may further include (as shown by the dashed box in FIG. 4), after removing the sample of sprayed/blended wood flakes, heating 410 the adhesive resin sprayed/blended wood flakes until spots of adhesive resin are substantially differentiable from the portion of the wood flakes that is not covered by adhesive resin (i.e., until the contrast between resin-coated and non-resin coated wood surfaces are enhanced). For example, the sample of adhesive resin-coated wood flakes may be heated at 250° F. for a predetermined time such as from about 15 minutes to 45 minutes. Measuring and analyzing 408 the high contrast image typically includes: determining an area of the adhesive resin spot/spots, determining a bare area of the wood flake on which the spot/spots are situated (the sum of these areas providing the total wood flake area), determining a percent coverage of the area of the wood flake by the adhesive resin spot/spots, and determining an average percent coverage area of a preselected number of wood flakes by the adhesive resin spots. Where desired (as shown in FIG. 4 by a dashed box), the method may include, after measuring and analyzing 408, a step of sending 412 the output of the analysis to a monitor screen of the computer, to a storage medium and/or to a printer. Clearly, the user may determine how many wood flakes are to be examined. In the example above, twelve wood flakes were used and has been found to be a suitable sample size for providing useful information of the performance of an adhesive resin blender. Experimentation has shown that a sample size of 20, where flakes are approximately one inch by three inches, works well with current blending techniques, and all the flakes fit on the scanner bed at the same time.

FIG. 5 is a flow chart showing another embodiment of steps in accordance with the method of the present invention. In this embodiment, the method includes the steps of: collecting 502 a sample of wood flakes blended with adhesive resin and output from the blender wherein the wood flakes are approximately at least 1 inch×2 inches; heating 504 at least 30 wood flakes for one minute at 350° F.; placing 506 twenty of the at least 30 wood flakes on a scanner bed; preview scanning 508 the wood flakes using at least 1200 dpi resolution with 1800 dpi interpolation while maximizing settings for color resolution and setting dimensions to a width of 0.5 inch and a length of 1.5 inches; starting 510 a macro for scanning and inputting a filename and an input number of wood flakes; scanning 512 an image of each wood flake; for each wood flake, adjusting 514 an exposure setting using an auto-setting for the wood flake, editing the image of the wood flake and copying the image, using image analysis software with resin analysis macros to determine data for a percentage coverage of the wood flake by the adhesive resin, and saving the data until all desired wood flakes have been processed; and importing 516 the data in data files and generating a report. It should be noted that, if the wood flakes are heated for more than one minute at 350° F., a fire may occur.

As shown in FIG. 6, the same process may be used to grade wood chips. That is, to test for suitability of adhesive resin bond for use in making wood-based veneer bonded composite products, the wood being considered for use may be sprayed and coated with a predetermined resin, then pressed and cured, soaked and pulled apart to determine rate of wood failure. The method is used for determining adhesive resin bond on wood samples pulled from a wood-based veneer composite that has been vacuum/water-soaked for a predetermined amount of time, to provide a grade for the wood-based veneer composite. The method includes the steps of: heating 602 the wood samples pulled from the wood-based veneer composite for one of: a predetermined time and until the wood samples are substantially dry; placing 604 said wood samples on a scanning bed; scanning 606 said wood samples using at least 1200 dpi resolution with 1800 dpi interpolation to provide image data; using 608 image analysis software with resin analysis macros installed on a computer wherein the image data of each wood sample is filtered to provide a high contrast image that shows adhesive resin differentiated from bare wood on which the adhesive resin is situated; and measuring and analyzing 610 the high contrast image, using the image analysis software with resin analysis macros, to provide an output showing at least a percent resin coverage/wood failure percentage of the wood sample.

The grade may also be based on at least one of: a selected cure time, a press time, a press temperature and the adhesive resin used to manufacture the wood-based veneer composite. Measuring and analyzing the high contrast image generally includes: determining an area of the adhesive resin spot/spots, determining an area of each wood sample on which the adhesive resin spot/spots are situated, determining a percent coverage of the area of the wood sample by the adhesive resin spot/spots, and determining an average percent coverage area of a preselected number of wood samples by the adhesive resin spots. After measuring and analyzing, the output is typically sent 612 to at least one of: a monitor screen of the computer, a storage medium and a printer.

Upon testing a desired number of samples of pressed wood veneer composites bonded by a selected resin for a particular cure time, press time and temperature, the data may be examined to determine a threshold failure point for the samples. Determining a failure point for the samples allows a grade to be predicted for bonding the wood veneer composites bonded using the selected resin and bonding technique.

Although the present invention has been described in relation to particular preferred embodiments thereof, many variations, equivalents, modifications and other uses will become apparent to those skilled in the art. It is preferred, therefore, that the present invention be limited not by the specific disclosure herein, but only by the appended claims.

What is claimed is:

1. A method for determining adhesive resin distribution on wood flakes to be formed into a wood-based composite, where an adhesive resin has been applied onto the wood flakes, said method comprising the steps of:

obtaining a sample of wood flakes having applied adhesive resin and placing the sample wood flakes on a scanning bed;

scanning the wood flakes using at least 1200 dpi resolution with 1800 dpi interpolation to provide image data;

using image analysis software with resin analysis macros installed on a computer wherein the image data of a wood flake is filtered to provide a high contrast image that shows each adhesive resin spot differentiated from a bare wood flake on which the adhesive resin spot is situated; and measuring and analyzing the high contrast image, using the image analysis software with resin analysis macros, to provide an output showing at least a percent coverage of the wood flake by the adhesive resin.

2. The method of claim 1 further including, after obtaining the sample of wood flakes having applied adhesive resin, heating the wood flakes until spots of adhesive resin are substantially differentiable from a portion of the wood flakes that is not covered by adhesive resin.

3. The method of claim 2 wherein the sample of wood flakes is heated at 250°.

4. The method of claim 3 wherein the sample of wood flakes is heated for a time between 15 minutes and 45 minutes.

5. The method of claim 1 wherein measuring and analyzing the high contrast image includes: determining an area of the adhesive resin spot/spots, determining an area of the wood flake on which the adhesive resin spot/spots are situated, determining a percent coverage of the area of the wood flake by the adhesive resin spot/spots, and determining an average percent coverage area of a preselected number of wood flakes by the adhesive resin spots.

6. The method of claim 1 further including, after measuring and analyzing, sending the output to at least one of: a monitor screen of the computer, a storage medium and a printer.

7. A system for determining adhesive resin distribution on adhesive resin blended wood flakes for wood-based composite production, comprising:

a flatbed scanner with at least 1200 dpi resolution with 1800 dpi interpolation, arranged to receive a sample of the adhesive resin blended wood flakes from output of a blender, for scanning the adhesive resin blended wood flakes to provide image data to image analysis software with resin analysis macros installed on a computer;

the image analysis software with resin analysis macros installed on the computer, arranged to receive the image data from the flatbed scanner, for filtering the image data to provide a high contrast image that shows each adhesive resin spot differentiated from a bare wood flake on which the adhesive resin spot is situated, measuring an area of each adhesive resin spot and the area of bare wood flake on which the adhesive resin spot is located and analyzing the image data to provide an output showing at least a percent coverage of the wood flake by the adhesive resin.

8. The system of claim 7 wherein the sample of adhesive resin blended wood flakes is heated until spots of adhesive resin are substantially differentiable from the wood flakes.

9. The system of claim 8 wherein the sample of blended wood flakes is heated prior to being scanned at 250° F.

10. The system of claim 9 wherein the sample of blended wood flakes is heated prior to being scanned for a time between 15 minutes and 45 minutes.

11. The system of claim 7 wherein the output is shown on a monitor of the computer.

12. The system of claim 7, further including a printer, coupled to the computer, for printing the output.

13. A method for determining adhesive resin distribution on wood flakes to be formed into a wood-based composite, where an adhesive resin has been applied onto the wood flakes, said method comprising the steps of:

collecting a sample of wood flakes blended with adhesive resin and output from the blender wherein the wood flakes are approximately at least 1 inch×2 inches;

heating at least 30 wood flakes for one minute at 350° F.;

placing at least twenty of the at least 30 wood flakes on a scanner bed;

preview scanning the wood flakes using at least 1200 dpi resolution with 1800 dpi interpolation while maximizing settings for color resolution and setting dimensions to a width of 0.5 inch and a length of 1.5 inches;

starting a macro for scanning and inputting a filename and an input number of wood flakes;

scanning an image of each wood flake;

for each wood flake, adjusting an exposure setting using an auto-setting for the wood flake, editing the image of the wood flake and copying the image, using image analysis software with resin analysis macros to determine data for a percentage coverage of the wood flake by the adhesive resin, and saving the data until all desired wood flakes have been processed; and importing the data in data files and generating a report.

14. A method for determining adhesive resin bond quality on wood samples pulled from a wood-based veneer composite that has been vacuum/water-soaked for a predetermined amount of time, to provide a grade for the wood-based veneer composite, said method comprising the steps of:

heating the wood flakes pulled from the wood-based composite for one of:
a predetermined time and until the wood flakes are substantially dry;
placing said wood samples on a scanning bed;
scanning said wood samples using at least 1200 dpi resolution with 1800 dpi interpolation to provide image data;
using image analysis software with resin analysis macros installed on a computer wherein the image data of each wood sample is filtered to provide a high contrast image that shows each adhesive resin spot differentiated from a bare wood on which the adhesive resin spot is situated; and measuring and analyzing the high contrast image, using the image analysis software with resin analysis macros, to provide an output showing at least a percent resin coverage/wood failure percentage of the wood sample.

15. The method of claim 14 wherein the grade is also based on at least one of a selected cure time, a press time, a press temperature and the adhesive resin used to manufacture the wood-based veneer composite.

16. The method of claim 14 wherein measuring and analyzing the high contrast image includes: determining an area of the adhesive resin spot/spots, determining an area of each wood sample on which the adhesive resin spot/spots are situated, determining a percent coverage of the area of the wood sample by the adhesive resin spot/spots, and determining an average percent coverage area of a preselected number of wood sample by the adhesive resin spots.

17. The method of claim 14 further including, after measuring and analyzing, sending the output to at least one of: a monitor screen of the computer, a storage medium and a printer.

* * * * *

UNITED STATES PATENT AND TRADEMARK OFFICE
CERTIFICATE OF CORRECTION

PATENT NO.    : 6,618,492 B1
DATED         : September 9, 2003
INVENTOR(S)   : James E. Romans It is certified that error appears in the above-identified patent and that said Letters Patent is hereby corrected as shown below:

<u>Title page,</u>
Item [*] Notice, "0 days" has been replaced with -- 384 days --.

Signed and Sealed this

Twenty-seventh Day of April, 2004

JON W. DUDAS
*Acting Director of the United States Patent and Trademark Office*